United States Patent [19]

Bernauer et al.

[11] 3,988,362

[45] Oct. 26, 1976

[54] INTERMEDIATES FOR PREPARATION OF 2,2,3-ENDOTRIMETHYL-7-ANTI-AMINO-NORBORNANES

[75] Inventors: Karl Bernauer, Allschwil; Janos Borgulya; Marc Montavon, both of Basel, all of Switzerland; Hermann Bretschneider; Kraft Hohenlohe-Oehringen, both of Innsbruck, both of Austria; Günter Weis, Igls, Austria

[73] Assignee: Hoffmann-La Roche Inc., Nutley, N.J.

[22] Filed: Feb. 28, 1975

[21] Appl. No.: 553,941

Related U.S. Application Data

[62] Division of Ser. No. 383,953, July 30, 1973, Pat. No. 3,884,976.

[30] Foreign Application Priority Data

Aug. 10, 1972 Switzerland............ 11844/72

[52] U.S. Cl. ............ 260/471 C; 260/556 AR; 260/557 R; 260/570.9

[51] Int. Cl.$^2$............ C07C 101/00; C07C 103/37; C07C 143/72

[58] Field of Search...... 260/556 AR, 570.9, 471 C, 260/557 R

[56] References Cited

UNITED STATES PATENTS 3,136,787   6/1964   Daeniker.................. 260/556 AR

*Primary Examiner*—Sam Rosen
*Attorney, Agent, or Firm*—Samuel L. Welt; George M. Gould

[57] ABSTRACT

The present disclosure relates to intermediates 2,2,3-endo-trimethyl-7-anti-amino-norbornanes and N-substituted analogs thereof. In particular the aforesaid compounds have a conventional protective group on the amino moiety and also hydroxymethyl or p-toluenesulfonyl oxymethyl groups in the 3-position.

5 Claims, No Drawings

INTERMEDIATES FOR PREPARATION OF 2,2,3-ENDOTRIMETHYL-7-ANTI-AMINO-NORBORNANES

This is a division of application Ser. No. 383,953 filed July 30, 1973, now U.S. Pat. No. 3,884,976.

DESCRIPTION OF THE INVENTION

The norbornane derivatives provided by the present invention are compounds of the general formula

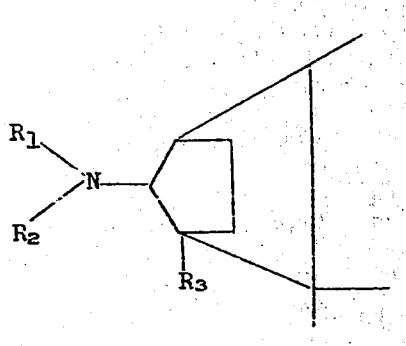

(I)

wherein $R_1$ and $R_2$ each independently is hydrogen lower alkyl, or lower alkenyl or $R_1$ and $R_2$ together with the nitrogen atom to which they are attached are a 5- or 6-membered heterocyclic group and $R_3$ is hydrogen or methyl
and acid addition salts thereof.

The term "lower alkyl" referred to in this specification and in the claims appended hereto are monovalent straight or branched chain saturated hydrocarbon radicals containing 1–7 carbon atoms (e.g., the methyl, ethyl, isopropyl, butyl, isobutyl, tertbutyl, pentyl and hexyl groups). Preferred lower alkyl groups are those containing 1–3 carbon atoms, especially the methyl group. The term "lower alkenyl" as used herein are monovalent straight or branched chain hydrocarbon radicals containing at least one ethylenic bond and from 2 to 7 carbon atoms (e.g., the vinyl, allyl and butenyl groups). The vinyl ad allyl groups are the preferred lower alkenyl groups. Examples of 5- or 6-membered heterocyclic groups formed by $R_1$ and $R_2$ together with the nitrogen atom to which they are attached are the pyrrolidino, piperidino and (lower alkyl)-substituted pyrrolidino and piperidino groups.

Preferred norbornane derivatives provided by the present invention comprise those in which $R_1$, $R_2$ and $R_3$ each are hydrogen.

The norbornane derivatives aforesaid (i.e., the compounds of formula I and their acid addition salts) are readily prepared by hydrogenating the methylene group of a compound of the general formula

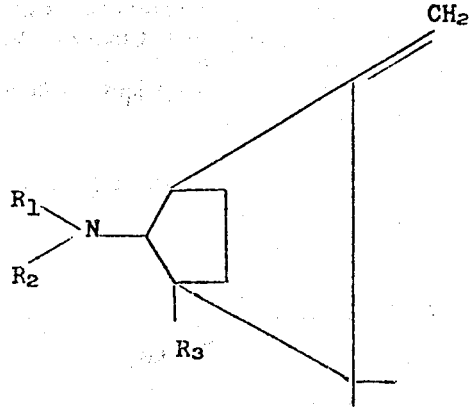

(II)

wherein $R_1$, $R_2$ and $R_3$ are as above
or of an acid addition salt thereof. Alternatively the compounds of formula I may be obtained by cleaving off the protecting group or protecting groups by solvolysis or reduction in a compound of the general formula

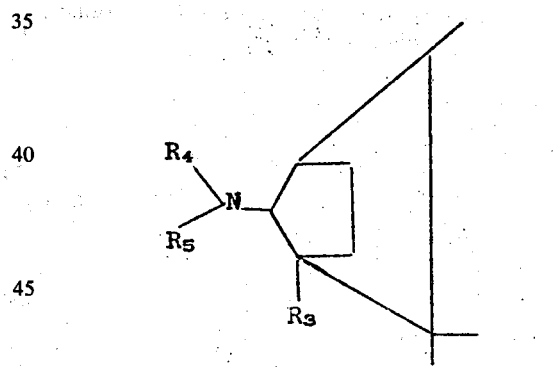

(III)

wherein $R_4$ is hydrogen or a protecting group cleavable by solvolysis or reduction and $R_5$ is a protecting group cleavable by solvolysis or reduction,
or in an acid addition salt of such a compound.

Compounds of formula I wherein $R_1$ and $R_2$ are lower alkyl or lower alkenyl are prepared by lower alkylating or lower alkenylating a primary amine thus obtained. Should a basic compound be obtained, it can be converted into an acid addition salt by methods known per se.

The starting materials of formula II in which $R_1$ and $R_2$ each are hydrogen can be prepared according to the following process sequence:

In the first step of the foregoing formula scheme, a compound of formula (a)

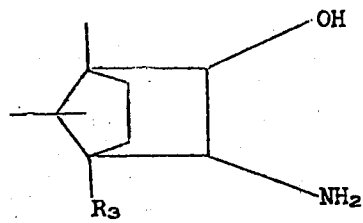

is formylated with methyl formate in the presence of catalytic amounts of formic acid. A resulting formamido compound of formula (b)

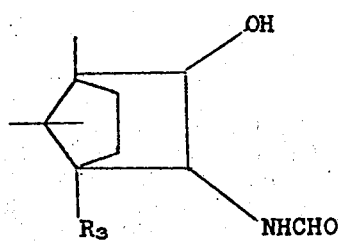

is then treated with thionyl chloride in ether and, after distillation of the ether, treated with isopropanol/water (3:1). By this procedure, an intermediately formed compound of formula (c)

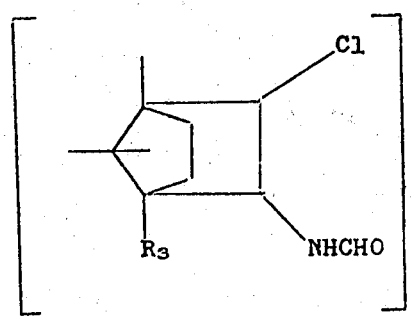

is converted into a compound of formula (d).

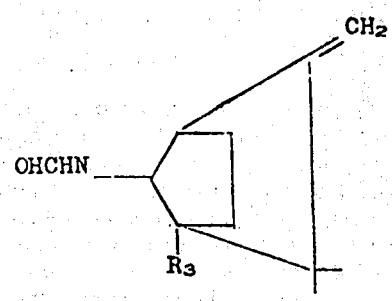

A compound of formula (d) is finally hydrolyzed, for example by boiling, if desired in an alkaline medium, to give a compound of formula (e)

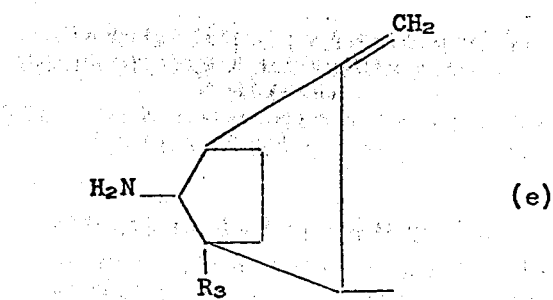

which corresponds to a compound of formula II in which $R_1$ and $R_2$ each are hydrogen.

Compounds of formula II in which $R_1$ and/or $R_2$ are other then hydrogen can be prepared from a compound of formula (e) by substitution at the nitrogen atom according to known methods; for example, by reaction with an appropriate alkyl or alkenyl halide.

Compounds of formula II in which $R_1$ and $R_2$ together with the nitrogen atom to which they are attached represent a 5- or 6-membered heterocyclic group can be prepared from a compound of formula (c) by formation of the appropriate heterocyclic ring according to methods known per se.

The preferred starting materials of formula II are those in which $R_1$, $R_2$ and $R_3$ each are hydrogen.

The hydrogenation of a compound of formula II or of an acid addition salt thereof can be carried out using activated hydrogen. The hydrogenation is expediently carried out catalytically using catalysts which are suitable for the hydrogenation of a methylene group to the methyl group (e.g., Raney nickel, platinum, rhodium or the like). This hydrogenation may be carried out in aqueous or alcoholic solution. Although the temperature at which the hydrogenation is carried out is not critical, a temperature between room temperature and 110° C (in a pressure vessel) is expedient.

The starting materials of formula III can also be prepared from the compounds of formula (a) hereinbefore by the introduction of one or two protecting groups at the nitrogen atom, treatment of the thus obtained compound with thionyl chloride in ether, hydrolysis of the intermediately formed chloro-substituted compound, conversion of the resulting methylene-substituted compound into the hydroxymethyl-substituted compound and conversion of the latter compound into the methyl-substituted compound. This procedure is illustrated in the following reaction sequence for the preparation of a compound of formula III in which $R_1$ is hydrogen and $R_5$ is the tosyl group. In this reaction sequence, $R_3$ has the significance given earlier and $TolSO_2$ represents the tosyl group.

In the first step of the sequence, a compound of formula (a)

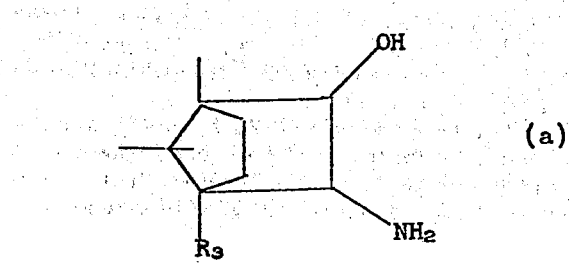

is converted by means of p-toluenesulphonyl chloride into a compound of formula (f)

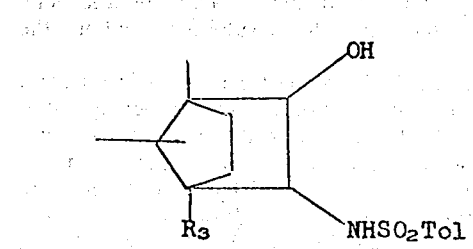

(f)

which, in turn, is converted by treatment with thionyl chloride and subsequent hydrolysis of an intermediately formed chloro compound of formula (g)

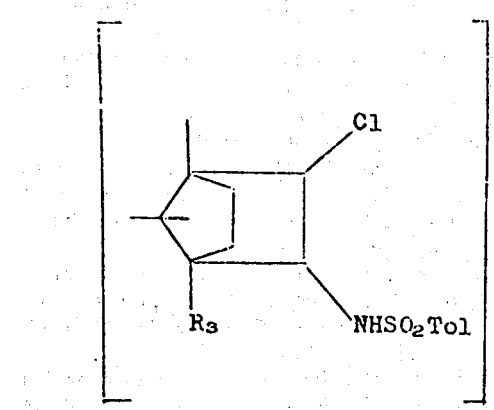

(g)

into a toluenesulphonylamido-camphene of formula (h)

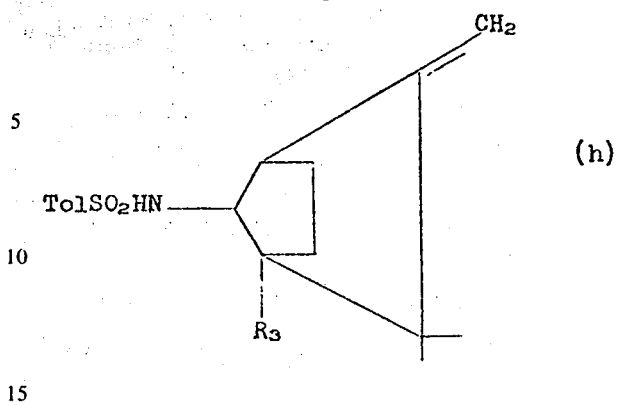

(h)

This compound is converted by treatment with diborane and subsequently with hydrogen peroxide/sodium hydroxide into a hydroxymethyl compound of formula (i)

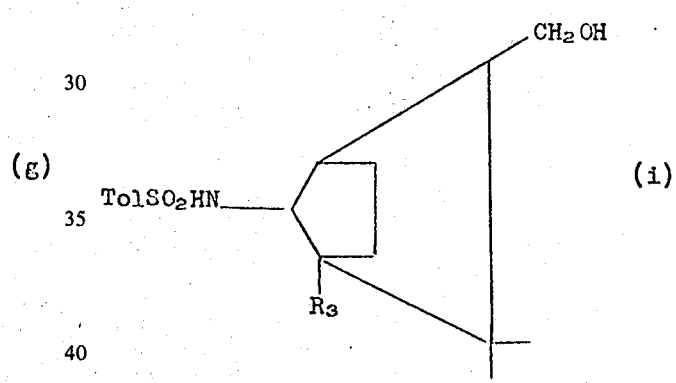

(i)

and this, in turn, is converted by treatment with tosyl chloride into a compound of formula (j)

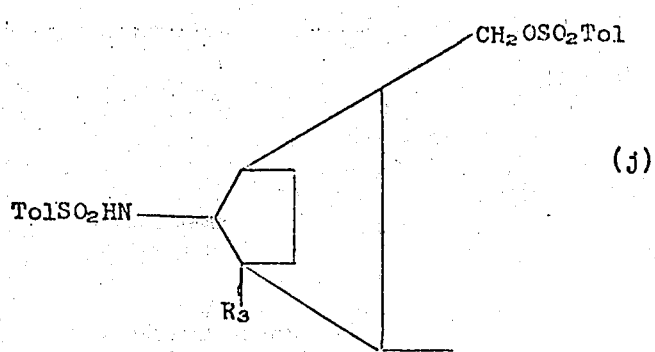

(j)

from which the tosyloxy group is then reductively cleaved off by means of lithium aluminum hydride to give a compound of formula (k)

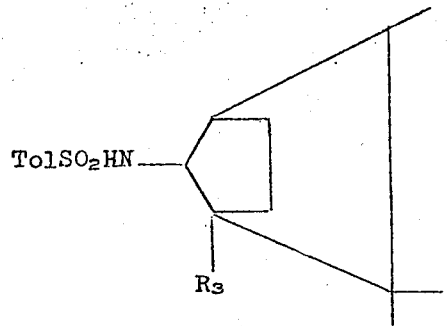

which corresponds to a compound of formula III in which $R_4$ is hydrogen and $R_5$ is tosyl.

The tosyl group is cleaved off from a compound of formula (k) in accordance with the present process to give a compound of formula I in which $R_1$ and $R_2$ each are hydrogen and $R_3$ is as above. The cleavage of the tosyl group can be carried out, for example, using sodium in liquid ammonia.

The preferred starting materials of formula III are those in which $R_3$ is hydrogen.

The protecting groups denoted by $R_4$ and/or $R_5$ can be any of the N-protecting groups commonly known in peptide chemistry. Examples of such groups are the benzyl group, which can be cleaved off by hydrogenation (e.g., by catalytic hydrogenation in the presence of palladium/carbon), carbalkoxy groups such as the carbomethoxy group or the carbobenzoxy group, which can be cleaved off by solvolysis (e.g., using acids such as hydrogen bromide in glacial acetic acid) or by hydrogenation (e.g., in the presence of palladium/carbon) and the formamido group which can be cleaved off by solvolysis either under acidic conditions (e.g., using a mineral acid such as hydrochloric acid) or under basic conditions (e.g., using sodium hydroxide). The foregoing cleavage methods are carried out under the usual conditions; for example, in solvents containing hydroxy groups such as lower alkanols or in aqueous solution. The temperature is not critical, although the cleavage is generally carried out at a temperature between room temperature and the boiling point of the mixture.

The primary amine obtained according to the present process can, if desired, be lower alkylated or lower alkenylated to give a compound of formula I in which $R_1$ and/or $R_2$ are lower alkyl or lower alkenyl. This lower alkylation or lower alkenylation can be carried out according to methods known per se; for example, by reacting the primary amine with a lower alkyl halide or a lower alkenyl halide, especially a chloride or iodide. A further N-alkylation procedure comprises reacting the primary amine with an aldehyde (e.g., formaldehyde) and reducing the product (e.g., with formic acid). Di(lower alkylation) can be expediently carried out using a dialkyl sulphate (e.g., dimethyl sulphate).

A base obtained can, if desired, be converted into an acid addition salt with an inorganic acid (e.g., hydrochloric acid, hydrobromic acid, sulphuric acid, phoshoric acid and the like) or with an organic acid (e.g., acetic acid, tartaric acid, maleic acid, fumaric acid, citric acid, oxalic acid, toluene-sulphonic acid and the like).

The compounds of formula I can occur in different stereoisomeric configurations. They can belong either to the syn- or to the anti-series, they can also be either endo- or exo-compounds and, moreover, they can also occur as racemates or in optically active form. The stereoisomerism of the compounds of formula I is governed by the steroisomerism of the starting materials used in their manufacture. Thus, for example, the compounds of the syn-series can be manufactured from the corresponding N-exo starting materials.

The norbornane derivatives of this invention (i.e., the compounds of formula I and their acid addition salts) have an anti-cataleptic activity and can be used for the treatment of Parkinsonism.

The anti-cataleptic activity can be determined according to the method of J. R. Boissier et al. [C.R. Soc. Biol. 158,2025–2028 (1964)]. In this test, for example, rac-2,2,3-endotrimethyl-7-anti-amino-norbornane hydrochloride has an $ED_{50}$ of 21 mg/kg i.p. and 50 mg/kg p.o. (in the rat).

Furthermore, the norbornane derivatives of this invention have a vericidal activity and can accordingly be used against virus infections, especially against influenza viruses [e.g., against influenza $A_2$ (Asia)].

In addition, the present norbornane derivatives have an antidepressant activity as has been determined in the barbiturate-potentiation test. They can accordingly be used as antidepressants.

The daily dose of the present norbornane derivatives is governed by the requirements of the patient to be treated and lies in the range of from about 50 mg to 300 mg, especially about 50-200 mg.

The toxicity of the norbornane derivatives provided by the present invention lies at about 300 mg to about 700 mg [$LD_{50}$ (p.o.); mouse]. For example, rac-2,2,3-endo-trimethyl-7-anti-amino-norbornane hydrochloride has an $LD_{50}$ (peroral administration in the mouse) of 700 mg/kg.

The compounds of formula I and their pharmaceutically acceptable acid addition salts can be used as medicaments in the form of pharmaceutical preparations which contain them in association with a compatible pharmaceutical carrier. This can be an organic or inorganic inert carrier material suitable for enteral or parenteral administration such as, for example, water, gelatine, gum arabic, lactose, starch, magnesium stearate, talc, vegetable oils, polyalkylene glycols, petroleum jelly etc. The pharmaceutical preparations can be made up in a solid form (e.g., as tablets, dragees, suppositories or capsules) or in a liquid form (e.g., as solutions, suspensions, syrups or emulsions). The pharmaceutical preparations may be sterilized and/or may contain adjuvants such as preservatives, stabilizers, wetting agents, emulsifiers, salts for variation of the osmotic pressure or buffers. They can also contain other therapeutically valuable substances.

The following Examples illustrate the process provided by the invention:

EXAMPLE 1

35.9 g of (1S)-2,2,3-endo-trimethyl-7-anti-(p-toluenesulphonylamido)-norbornane are dissolved in 600 ml of liquid ammonia and there are introduced into the solution with stirring 13.5 g of metallic sodium in small pieces, whereupon the solution remains blue for one hour. The excess sodium is decomposed with 32 g of ammonium chloride and, after about 3 hours, the ammonia is evaporated off. The residue is carefully taken up with 300 ml of ether and 100 ml of 5-N sodium hydroxide. The alkaline solution is extracted another three times with ether. The combined ethereal phases (about 1500 ml) are dried over sodium sulphate and the ether is distilled off. The residue is mixed with a small amount of solid potassium hydroxide and distilled under reduced pressure (14 mm). A fore-run of 0.6 g (bath temperature 80°–120° C, boiling point 30°–80° C) is rejected. The bulk of 6.9 g ($n_{25}° = 1.4812$) is obtained at a bath temperature of 120°–130° C, boiling point 85°–90° C.

The alkaline mother liquor is extracted with ether, the obtained extract distilled and the distillation residue extracted again with ether. Both ethereal phases are combined, dried and their residue is distilled in a bulb tube. The resulting distillate (1.4g) is combined with the bulk. There are obtained 8.3 g of (1S)-2,2,3-endo-trimethyl-7-anti-amino-norbornane.

This base is dissolved in 200 ml of absolute ether and ethereal hydrochloric acid is added dropwise with ice cooling until complete precipitation of the hydrochloride occurs. After recrystallization from 100 ml of acetone and about 2 ml of water, there are obtained 7.1 g of the hydrochloride.

For analysis, the hydrochloride is recrystallized twice from acetone/water.

$C_{10}H_{20}NCl$ (189.73): Calculated: C 63.31; H 10.63; N 7.38; Cl 18.69. Found: C 63.80; H 10.72; N 7.29; Cl 18.84. Decomposition point: over 300° C.

The analysis showed a water content of 2.08%. The values given above were calculated on the anhydrous compound.

| IR (KBr): | 3.38 | 6.65 | |
|---|---|---|---|
| NMR (DMSO): | —$NH_3$ | 8.11 | (wide, exchangeable with $D_2O$) |
| | $H_7$ | 3.27 | (s) |
| | 2 × 2$CH_3$ | 0.92 | (s)  0.75 (s) |
| | 3$CH_3$ | 0.74 | (d, $^JCH_3,H_3 = 7$ Hz) |

The (1S)-2,2,3-endo-trimethyl-7-anti-(p-toluenesulphonylamido)-norbornane used as the starting material can be obtained as follows:

85 g of (1R)-3-endo-amino-isoborneol are suspended in 400 ml of absolute ether and a solution of 47.5 g of p-toluenesulphonyl chloride is slowly added dropwise with vigorous stirring. The mixture is then stirred for a further 6 hours at room temperature. The resulting (1R)-3-endo-amino-isoborneol hydrochloride is filtered off, by which means the moiety of the base employed is recovered. There are obtained 47.3 g of the hydrochloride.

A solution of 30 ml of pure thionyl chloride in 100 ml of absolute ether is added dropwise, with stirring, to the ethereal phase. If tosylamido-isoborneol recrystallizes from the ethereal phase before the addition of the thionyl chloride, the mixture can be slightly warmed. After the addition, the ethereal phase is left to stand for 12 hours.

After 12 hours, the ether and excess thionyl chloride are distilled off.

The residue of the ethereal phase is dissolved in 250 ml of acetone and mixed, with warming, with 80 ml of water. The solution is left to stand for one hour on a water bath and then the solvent is distilled off. There is obtained a crude product (contaminated with resin fractions) from which the (1S)-7-anti-(p-toluenesulphonylamido)-camphene can be obtained by extraction with petroleum ether (40°–60° C). Yield: 54 g: m.p. 120°–123° C. 170 ml of boron fluoride etherate are slowly added dropwise, during 2 hours, to a well-stirred suspension of 28 g. of sodium borohydride in 200 ml of absolute tetrahydrofuran, boiling under reflux. The resulting diborane is conducted by means of a nitrogen stream into an ice-cooled receiver with 61 g of (1S)-7-anti-(p-toluenesulphonylamido)-camphene in 250 ml of absolute tetrahydrofuran. The contents of this receiver are stirred and the receiver is also connected to a washing bottle filled with acetone in order to bind the unreacted diborane. After 2 hours, the receiver is separated from the apparatus, provided with a calcium chloride tube and left to stand for 12 hours at room temperature. Then, the excess diborane is decomposed by the addition of ice (vigorous effervescence) and, with ice cooling and stirring, 270 ml. of 3-N sodium hydroxide and 75 ml of hydrogen peroxide (30%) are added dropwise. The mixture is subsequently stirred for 5 hours at room temperature and is then added dropwise with vigorous stirring, to 100 ml of concentrated hydrochloric acid and 1000 ml of ice. The precipitate which thus separates is extracted several times with a total of 1200 ml of ethyl acetate. The extract is washed acid-free with sodium bicarbonate solution, dried over sodium sulphate and evaporated for 2 hours at 70° C under reduced pressure. There is obtained (IS)-2,2-dimethyl-3-endo-hydroxymethyl-7-anti-(p-toluenesulphonylamido)-norbornane in the form of a non-crystalline residue (62.3 g).

For analysis, the compund is recrystallized twice from ether.

| $C_{17}H_{25}NO_3S$ | (323.45) | | | |
|---|---|---|---|---|
| Calculated: | C63.13 | H 7.79 | N 4.33 | S 9.92 |
| Found : | 63.36 | 7.92 | 4.34 | 10.06 |
| Melting Point: | 82°–88° C. | | | |
| IR (KBr): | 2.84 | 3.05 | 8.62 | |
| NMR ($CDCl_3$): | | | | |
| NH | 6.23 (d, $^JNH,H_7 = 6$ Hz) exchangeable with $D_2O$ | | | |
| $H_7$ | 3.49 (masked) | | | |
| —$CH_2$—O | 3.51 (d, $^JCH_2,H_3 = 7.5$ Hz) | | | |
| $CH_3$—Ar | 2.40 (s) | | | |
| OH | 1.83 (s, exchangeable with $D_2O$) | | | |
| 2 × $CH_3$ | 0.91 (s)  0.77 (s). | | | |

62.3 g of the non-crystalline residue obtained after evaporation of the ethyl acetate extract are dissolved in 500 ml of pyridine, which has been freshly distilled from potassium hydroxide, and mixed at 0° C with 73.5 g of tosyl chloride. While the mixture is being kept for 3 days at 0° C, long needles of the pyridine hydrochloride crystallize out. The mixture is then poured on to about 1200 ml of ice and 600 ml of ethyl acetate with vigorous stirring and mixed to a constant acidic reaction with concentrated hydrochloric acid (about 350 ml). The ethyl acetate phase is isolated and the acidic aqueous phase is again extracted with 200 ml of ethyl acetate. The combined ethyl acetate phases are washed twice with water, dried over sodium sulphate and evaporated. Care is maintained that the temperature of the mixture does not rise above 0° C until the isolation of the ethyl acetate phase is carried out.

The evaporation residue (90.1 g) is dissolved in 60 ml of ethyl acetate and mixed with warming, with 120 ml of absolute ether. After standing for 24 hours at 0°, there can be filtered off 38.6 g of crystalline (1S)-2,2-dimethyl-3-endo-(p-toluenesulphonyloxymethyl)-7-anti-(p-toluenesulphonylamido)-norbornane of melting point 129°–132° C.

The evaporation residue of the mother liquor (38.0 g) is again tosylated in pyridine as described earlier. The working up yields a further 11.8 g of a substance with a melting point of 124°–130° C.

For analysis, the compound is recrystallized twice from ethyl acetate/ether (1:2).

| $C_{24}H_{31}NO_5S_3$ | (477.65) | | | |
|---|---|---|---|---|
| Calculated: | C 60.35 | H 6.54 | N 2.93 | S 13.43 |
| Found : | 60.23 | 6.56 | 2.86 | 13.42 |
| Melting Point: | 133°–135° C. | | | |
| IR (KBr): | 3.10 | 8.55 | 11.37 | |
| NMR (DMSO): | | | | |
| NH | Superimposed by H-aromatic. | | | |
| —O—CH$_2$— | 3.94 (d, $^JCH_2,H_3 = 7.5$ Hz) | | | |
| H$_7$ | 3.15 (d, becomes a singlet after exchange with D$_2$O) | | | |
| 2 × AR—CH$_3$ | 2.41 | | | |
| 2 × CH$_3$ | 0.81 (s) 0.69 (s) | | | |

38.6 g of (1S)-2,2-dimethyl-3-endo-(p-toluenesulphonyloxymethyl)-7-anti-(p-toluenesulphonylamido)-norbornane are dissolved in 125 ml of absolute tetrahydrofuran and added dropwise, with stirring, to a suspension of 6 g of lithium aluminum hydride in 275 ml of absolute tetrahydrofuran. After the addition, the mixture is boiled under reflux for 5 hours. After cooling, the excess lithium aluminum hydride is carefully decomposed with water and the mixture is left to stand for 12 hours. It is then filtered and the solvent removed. The residue (27.5 g) forms a hard mass, which is then dissolved in 100 ml of ethanol and mixed, with warming, with 50 ml of water. The (1S)-2,2,3-endo-trimethyl-7-anti-(p-toluenesulphonylamido)-norbornane formed separates firstly as an oil, but crystallizes out in the course of 12 hours at 0° C. Yield: 24.6 g: boiling point 108°–111° C.

For analysis, the compound is recrystallized twice from ethanol/water.

| $C_{17}H_{25}NO_2S$ | (307.46) | | | |
|---|---|---|---|---|
| Calculated: | C 66.41 | H 8.20 | N 4.56 | S 10.43 |
| Found : | 66.24 | 8.18 | 4.45 | 10.04 |
| Melting Point: | 110°–113° C. | | | |
| IR (KBr): | 3.04 | 7.55 | 9.47 | |
| NMR (CCl$_4$): | | | | |
| NH | 5.80 (d, $^JNH,H_7 = 6$ Hz) | | | |
| H$_7$ | 3.37 (d, $^JNH,H_7 = 6$ Hz) becomes a singlet with double resonance on NH with exchange of NH with D$_2$O | | | |
| Ar—CH$_3$ | 2.43 (s) | | | |
| 2 × 2CH$_3$ | 0.88 (s) 0.73 (s) | | | |

| -continued | |
|---|---|
| 1 × 3CH$_3$ | 0.72 (d, $^JCH3,H_3 = 7$ Hz). |

EXAMPLE 2

5 g of the (1S)-2,2,3-endo-trimethyl-7-anti-amino-norbornane obtained according to Example 1 are heated with 50 ml of formic acid and 20 ml of 35% formalin for 24 hours on a water bath. The cooled reaction mixture is treated with 10 ml of concentrated hydrochloric acid and evaporated on a rotary evaporator. The crystalline evaporation residue is suspended in acetone, filtered, dissolved in water and again brought to crystallization by the addition of acetone. There are obtained 6.2 g of (1S)-2,2,3-endo-pentamethyl-7-anti-amino-norbornane hydrochloride of melting point 276° C (with decomposition).

| $C_{12}H_{23}N.HCl$ | (217.78) | | |
|---|---|---|---|
| Calculated: | C 66.18 | H 11.11 | N 6.44 |
| Found : | 66.35 | 11.30 | 6.41 |

EXAMPLE 3

10 g of the (1S)-2,2,3-endo-trimethyl-7-anti-amino-norbornane obtained according to Example 1 are introduced, with external ice cooling, into formacetic anhydride (prepared from 30 ml of formic acid and 45 ml of acetic anhydride after standing for 2 hours at room temperature). After the addition, the mixture is brought to room temperature and evaporated under reduced pressure. The residue is partitioned between ether and soda solution. The organic phase is dried, evaporated, dissolved in 20 ml of tetrahydrofuran and added 3 g of lithium aluminum hydride in 150 ml of tetrahydrofuran. After boiling for 2 hours under reflux, the mixture is decomposed by the dropwise addition of 20 ml of water, filtered and the residue of the filtrate precipitated from ethereal solution using ether/hydrochloric acid. After recrystallization from water/acetone, there is obtained (1S) 2,2,3-endo-tetramethyl-7-anti-amino-norbornane hydrochloride (11.1 g) of melting point 320°–330° C (decomposition).

| $C_{11}H_{22}NCl$ | (203.76) | | | |
|---|---|---|---|---|
| Calculated: | C 64.84 | H 10.88 | N 6.88 | Cl 17.40 |
| Found : | 65.07 | 10.90 | 6.88 | 17.29 |

EXAMPLE 4

5 g of the (1S)-2,2,3-endo-trimethyl-7-anti-amino-norbornane obtained according to Example 1 are reacted in 15 ml of methylene chloride with 2.7 g of allyl chloride at room temperature. After 24 hours, the hydrochloride of the base employed is precipitated by the addition of ether. It is filtered off and the filtrate evaporated under reduced pressure. The residue is dissolved in ether and precipitated using ether/hydrochloric acid. The basic constituents precipitated as hydrochlorides (3.8 g) are boiled in 150 ml of acetone and filtered while hot. There are obtained 1.3 g of (1S) 2,2,3-endo-trimethyl-7-anti-amino-norbornane hydrocloride of melting point 285° C (decomposition). For analysis, the hydrochloride is purified (unchanged decomposition point) by recrystallization from water/acetone.

| $C_{13}H_{27}NCl$ | (229.79) | | | |
|---|---|---|---|---|
| Calculated: | C 67.94 | H 10.53 | N 6.10 | Cl 15.43 |
| Found : | 68.19 | 10.65 | 6.08 | 15.64 |

EXAMPLE 5

1 g of (1S)-7-anti-amino-camphene is dissolved in 40 ml of absolute ethanol and hydrogenated with hydrogen in the presence of about 200 mg of Raney nickel for 15 hours at room temperature (24° C) and 150 atmospheres in a shaking autoclave. Then the hydrogenation product is filtered from the catalyst under a vacuum, the filtrate made congo-acid with alcoholic hydrochloric acid and evaporated. The residue is dissolved in water and the amine liberated with sodium hydroxide. The separated base is taken up in ether and the ethereal solution washed with water, dried over sodium sulphate and concentrated. The 2,2,3-endo-trimethyl-7-anti-amino-norbornane obtained distills in a bulb tube (air bath) at 100°–150° C and 18 mm. Yield: 938.1 mg.

The 60 MHz spectrum shows that the free base contains at least 95% of the endo compound and at the most 5% of the isomeric 3-exo-methyl compound.

The starting material can be prepared as follows:

27.6 g of (1S)-7-anti-(p-toluenesulphonylamido)-camphene (prepared according to the relevant details in Example 1) are introduced into about 300 ml of liquid ammonia and sodium metal is added in small pieces until the blue coloration of the solution persists for 0.5 hour (about 9.8 g of sodium). Then 24 g (10% excess) of ammonium chloride corresponding to the amount of sodium, are added and the ammonia is evaporated. The solid residue is carefully taken up with moist ether (about 200 ml), the same amount of water added and a further 20 ml of 5-N sodium hydroxide added. The ethereal phase is isolated, the alkaline phase extracted a further twice, the combined ethereal phases dried and the ether evaporated. The residue from the ethereal phase is vacuum-distilled under nitrogen.

Yield: 9.9 g; boiling point at 14 mm: 98°–104° C (bath temperature 135°–145° C); $(\alpha)_{CH_3OH} = 54.35°$; $n_{22°} = 1.4974$.

EXAMPLE 6

500 mg of (1S)-7-anti-amino-camphene hydrochloride are dissolved in 25 ml of water and hydrogenated in the presence of about 100 mg of Raney nickel at room temperature in a semimicro hydrogenation apparatus. The theoretical amount of hydrogen (59.7 ml) is taken up during about 22 hours. Then the hydrogenation product is filtered off from the catalyst under a vacuum and the (1S)-2,2,3endo-trimethyl-7-anti-amino-norbornane is liberated from the filtrate with sodium hydroxide. This base is taken up in ether, the ether solution washed with water, dried over sodium sulphate and filtered. The filtrate is treated with alcoholic hydrochoric acid, evaporated and the corresponding hydrochloride crystallized from alcohol/ether. Melting point: over 300° C; yield: 400 mg; $[\alpha]_D^{25°} = -3.6°$ (c = 1.0 in ethanol).

EXAMPLE 7

22.4 g of (1R)-7-anti-amino-camphene hydrochloride are dissolved in 400 ml of absolute ethanol and hydrogenated in the presence of 4 g of Raney nickel for 15 hours at 100° C and 150 atmospheres of hydrogen. Then the hydrogenation product is separated from the catalyst, the filtrate treated with 30 ml of alcoholic hydrochloric acid and the solution evaporated. The residue is dissolved in 200 ml of water and extracted twice with 50 ml of ether each time. The clear aqueous phase is adjusted to pH 11 with 3-N sodium hydroxide, the separated base is taken up in ether and the ethereal solution is washed with saturated sodium chloride solution, dried over sodium sulphate, filtered and evaporated. The crude residue, which weighs 17.5 g is purified via the acetate as follows:

The crude base (17.5 g) is dissolved in 400 ml of absolute ether and treated dropwise with a solution of 4.8 g of glacial acetic acid in 50 ml of absolute ether with stirring. During the addition, the acetate precipitates. After about 10 minutes, the crystals are filtered off under a vacuum, washed with about 200 ml of ether and dried. 14 g of dry acetate are dissolved in water, the solution is adjusted to pH 11 with 3-N sodium hydroxide solution and the liberated base is extracted with ether. The ethereal solution is washed with saturated sodium chloride solution, dried over sodium sulphate, filtered and the filtrate is made congo-acid with alcoholic hydrochloric acid. In so doing, the hydrochloride of the (1R)-2,2,3-endo-trimethyl-7-anti-aminonorbornane precipitates as a crystallisate. The crystalline suspension is evaporated, the residue is evaporated with toluene and once with alcohol and the hydrochloride is crystallized from alcohol/ether. There are obtained 10.6 g of the hydrochloride with a melting point above 250° C (decomposition). From the mother liquor, a further 1.7 g of a salt with a melting point above 250° C (decomposition) are isolated. The total yield is therefore 12.3 g; $[\alpha]_D^{25°} = +1.2°$ (c = 1.0 in ethanol).

The starting material can be prepared as follows:

To 100 g of sodium amide (suspended in toluene) is added a solution of 177 g of (1S)-camphor in 1.63 liters of absolute toluene. The mixture is stirred under argon gassing for about 3 hours at room temperature, the contents of the flask are cooled to about 15° C and, within 60 minutes, 149.6 g of isoamyl nitrite are added dropwise so that the temperature of the mixture does not rise about 25° C. After stirring overnight at room tempeature, the mixture is cooled to about 5° C and treated dropwise, with stirring, with 1.3 liters of water. The toluene phase is carefully separated, the aqueous/alkaline phase is stirred well a further twice with 300 ml of toluene each time and the toluene is removed under suction each time. Subsequently, a solution of 286 g of sodium hydroxide in 216 ml of water is added with stirring to the aqueous-alkaline solution of the sodium isonitroso-camphor formed.

251 g of zinc powder are then added portionwise in such a manner that the internal temperature does not exceed 65° C. After the addition of the zinc powder, the mixture is stirred for a further 30 minutes at 65° c, cooled down to room temperature and covered with 500 ml of ether. The mixture is filtered under a vacuum and rinsed with about 500 ml of ether. The aqueous phase is separated and shaken out three times with 200 ml of ether each time. The combined ethereal phases are dried over potassium carbonate, filtered and evaporated. The residue is evaporated twice with 200 ml of benzene each time. The crude residue is (1S)-3-endo-amino-camphor weighs 160 g.

160 g of crude (IS)-3-endo-amino-camphor are hydrogenated for 12 hours in 450 ml of methanol in the presence of 30 g of Raney nickel at 90° C and 80 atmospheres of hydrogen. The hydrogenation product is filtered off from the catalyst under a vacuum, washed with 150 ml of methanol and the filtrate evaporated. The residue is dissolved in 600 ml of ether, washed three times with 100 ml of water each time and the ethereal solution is dried over sodium sulphate, filtered and evaporated. After recrystallization from 500 ml of n-hexane, there are obtained 110 g of (1S)-3-endo-amino-2-exo-borneol of melting point 190°–191° C; $[\alpha]_D^{25} = +3.2°$ ($c = 2.6$ in methanol). (The product is contaminated with about 10% of (1S)-3-endo-amino-2-endo-borneol). 84.5 g of (1S)-3-endo-amino-2-exo-isoborneol are suspended in 420 ml of methyl formate, treated with 0.6 ml of formic acid and boiled under reflux with stirring for 3 hours. Then the suspension is stirred for 17 hours at room temperature. Then the mixture is evaporated and the residue crystallized from alcohol/n-hexane. The crystals are filtered off, washed with n-hexane and dried. 52.9 g of (1S)-(2-exo-hydroxy-3-endo-bornyl)-formamide are obtained in the form of a white crystallisate of melting point 159°–160° C. From the mother liquor a further 28.7 g of formamido compound can be isolated. Total yield: 81.6 g; $[\alpha]_D^{25} = -42.2°$ ($c = 1.0$ in alcohol).

81.0 g of (1S)-(2-exo-hydroxy-3-endo-bornyl)-formamide are suspended in 410 ml of absolute ether and treated dropwise, with stirring at room temperature for 40 minutes, with 54.2 g of thionyl cloride (distilled over linseed oil). The mixture is subsequently stirred for 22 hours at room temperature. Subsequently, about 300 ml of ether are distilled off from the mixture, the residue is treated with 300 ml of water and 500 ml of isopropyl alcohol and the yellow solution is boiled under reflux for 6 hours. The isopropanol is then evaporated and the residue partitioned between ether and water. The aqueous solution is adjusted to pH 11 with 100 ml of concentrated sodium hydroxide and the liberated base is extracted with ether. The ethereal solution is washed with saturated sodium chloride solution, dried over sodium sulphate, filtered and the filtrate made congo-acid with 100 ml of alcoholic hydrochloric acid. In so doing, the hydrochloride of (1R)-7-anti-amino-camphene precipitates. The suspension is evaporated, the residue evaporated twice with toluene and the hydrochloride crystallized from alcohol/ether. After filtration under a vacuum and drying, there are obtained 49.9 g of the hydrochloride salt of melting point 270°–271° C. From the mother liquor a further 14.3 g of hydrochloride of melting point 269°–271° C. are isolated. The total yield of (1R)-7-anti-amino-camphene hydrochloride or (1R)-2,2-dimethyl-3-methylene-7-anti-amino-norbornane hydrochloride therefore amounts to 64.2 g; $[\alpha]_D^{25} = -48.6°$ ($c = 1.0$ in water).

EXAMPLE 8

138.6 g of rac-7-anti-amino-camphene hydrochloride are dissolved in 1380 ml of deionised water and hydrogenated in the presence of 33 g of Raney nickel for 20 hours at room temperature and subsequently hydrogenated for 6 hours at 80°–85° C and 90 atmospheres of hydrogen in a 5 liter shaking autoclave with a glass insert. After cooling, the catalyst is filtered off from the solution, washed with 400 ml of deionised water and the filtrate made alkaline (pH 11) with 200 ml of concentrated sodium hydroxide. The separated base is extracted three times with 250 ml of ether each time and the ethereal solution washed four times with 200 ml of saturated sodium chloride solution each time. The aqueous phases are extracted again with 250 ml of ether. The combined ethereal solutions are dried over sodium sulphate and filtered.

The filtrate obtained is made congo-acid with 200 ml of alcoholic hydrochloric acid. In so doing the hydrochloride of rac-2,2,3-endo-trimethyl-7-anti-amino-norbornane [rac-7-anti-amino-camphene] precipitates. The crystalline suspension is evaporated, the residue evaporated three times with 300 ml of toluene each time and once with 500 ml of alcohol. The crude hydrochloride is dissolved in 250 ml of warm ethanol at about 60° C and treated portionwise, with agitation, with 500 ml of ether. After standing for one hour at room temperature, the crystals are filtered off, washed twice with 150 ml of ether each time and dried for one hour at 90° C in a vacuum drying cupboard at 10 Torr. Yield: 101.3 g; melting point: above 300° C.

The starting material can be prepared as follows:

169.2 g of rac-3-endo-amino-isoborneol are suspended in 1000 ml of methyl formate, treated with 1 ml of formic acid and boiled under reflux with stirring for 90 minutes. Then the suspension is stirred at room temperature for 17 hours. Subsequently the methyl formate is evaporated off, the crystalline residue dissolved in 700 ml of hot ethanol and treated portionwise with n-hexane. In order to complete the crystallization, the mixture is left to stand for about 2 hours at 5° C. The crystals are filtered off, washed twice with 300 ml of n-hexane each time and dried in a vacuum drying cupboard at 65°–70° C and 10 Torr for 17 hours. There are obtained 149.7 g of rac-N-(2-exo-hydroxy-3-endo-bornyl)-formamide (white crystals) of melting point 179°–180° C. The mother liquor is evaporated to about 200 ml and treated with 400 ml of n-hexane. After filtering and drying, there are obtained 32.4 g of crystals of melting point 178°–180° C. Total yield of rac-N-(2-exo-hydroxy-3-endo-bornyl)-formamide: 182.1 g.

178.1 g of the foregoing formamido compound are suspended in 1200 ml of absolute ether and treated dropwise, with stirring at room temperature for 25 minutes, with 118.1 g of thionyl chloride (distilled over linseed oil). The mixture warms up from 21° C to 32° C during the addition and it forms a viscous mass (after the addition of about 35 ml of thionyl chloride) which gradually dissolves (after the addition of about 50 ml of thionyl chloride). A yellow solution is obtained. About 5 minutes after the addition of thionyl chloride, a white precipitate slowly separates and a suspension is obtained. Subsequently, this suspension is stirred for 18 hours at room temperature, then about 1000 ml of ether are distilled off from the mixture, the residue is mixed with 900 ml of isopropyl alcohol and 300 ml of deionised water and boiled under reflux for 6 hours (internal temperature about 55° C). The pH value of the solution is 1. The isopropyl alcohol is evaporated on a rotary evaporator at 50° C, the residue partitioned between 1000 ml of ether and 500 ml of deionised water and the ethereal solution is washed four times with 500 ml of deionised water each time and 200 ml of saturated sodium bicarbonate solution. The washing water phases are rinsed with 500 ml of ether. The combined ether phases are dried over sodium sulphate, filtered and evaporated. The brown-yellow oily residue consists of non-saponified rac-N-(2,2-dimethyl-3-methylene-7-anti-norbornyl)-formamide. Amount isolated: 27.2 g.

All the washing water phases are combined and adjusted to pH 11, in the presence of about 500 g of ice, with 200 ml of concentrated sodium hydroxide. The separated base is taken up with 1000 ml of ether and the aqueous phase extracted twice with 1000 ml of ether each time. The combined ether phases are washed three times with 750 ml of saturated sodium chloride solution each time, then dried over sodium sulphate and filtered. The filtrate is made congo-acid by the portionwise addition of 200 ml of alcoholic hydrochloric acid. In so doing, the hydrochloride salt precipitates. The suspension is evaporated on a rotary evaporator at a 50° C bath temperature, the residue evaporated twice with 500 ml of toluene each time and the hydrochloride of rac-7-anti-amino-camphene [rac-2,2-dimethyl-3-methylene-7-anti-amino-norbornane] is crystallized from 300 ml of warm ethanol and 1000 ml of ether. After filtration, the crystals are dried at 70° C and 10 Torr. There are obtained 102.1 g of rac-7-anti-amino-camphene hydrochloride of melting point 264°–265° C (decomposition). From the mother liquor a further 17.3 g of hydrochloride of melting point 263°–264° C (decomposition) are obtained.

The rac-7-anti-amino-camphene can also be prepared as follows:

2.057 g of rac-3-endo-amino-2-exo-borneol are dissolved in 40 ml of methylene chloride and 10 ml of acetonitrile and cooled to 0° C with an ice bath. 1.71 g of benzyl chloroformate are added thereto with stirring. Subsequently, a solution of 2.13 of triethylamine in 10 ml of methylene chloride is added dropwise and the mixture boiled under reflux for one hour, then the mixture is cooled down and washed successively with water, 1-N-hydrochloric acid and water, dried over sodium sulphate, filtered and evaporated. The viscous oily residue is distilled in a bulb tube (air bath at 150°–155° C and 0.001 Torr. Yield: 2.8 g of rac-3-endo-carbobenzoxyamido-2-exo-bornanol.

1.39 g of rac-3-endo-carbobenzoxyamido-2-exo-bornanol are dissolved in 4 ml of absolute ether and treated, with stirring at room temperature, with 0.66 g of thionyl chloride (distilled over linseed oil). The mixture is subsequently stirred for 16 hours. Then the ether is distilled off and the oily residue is mixed with 50 ml of acetone and 15 ml of water. The mixture is boiled under reflux for one hour. Subsequently the solution is evaporated, the residue dissolved in methylene chloride, washed with water, dried over sodium sulphate, filtered and evaporated. The viscous residue distills in a bulb tube (air bath) at 142°–147° C and 0.01 Torr. Yield: 1.2 g of rac-2,2-dimethyl-3-methylene-7-anti-carbobenzoxyamido-norbornane.

To 142.7 g of rac-2,2-dimethyl-3-methylene-7-anti-carbobenzoxyamido-norbornane in 1500 ml of liquid ammonia there are added portionwise during 60 minutes 24 g of sodium in small pieces. The color of the solution remains blue for one hour. Then 1 g of ammonium chloride is added in order to decompose the excess sodium. The mixture is treated with 400 ml of ether and the ammonia allowed to excape. The residue is partitioned between ether and water, made acidic with 3-N hydrochloric acid, separated and the ether washed with water. The combined aqueous phases are made alkaline with 3-N sodium hydroxide and the liberated base, rac-7-anti-amino-camphene [rac-2,2-dimethyl-3-methylene-7-anti-amino-norbornane], is extracted with ether. The ethereal solution is washed with water, dried over sodium sulphate, filtered and evaporated. The residue is distilled under reduced pressure. After removal of a fore-run, the bulk is distilled at 75°–76° C and 9 Torr. Yield: 37.5 g.

EXAMPLE 9

13,3 g of rac-1,2,2-trimethyl-3-methylene-7-anti-amino-norborane-hydroacetate are hydrogenated in a mixture of 270 ml of absolute benzene and 150 ml of n-butylacetate in the presence of 3,2 g of a palladium-bariumsulfate catalyst (5% palladium) at normal pressure and at room temperature. The catalyst is then filtered off, washed with benzene and the filtrate is concentrated by evaporation. The resulting turbid residue is dissolved in methylene chloride and the resulting solution is filtered through kieselgur. The clear filtrate is evaporated rated and the residue dissolved in water and made alkaline by means of 3 N sodium hydroxide. The resulting free base is taken up in methylene chloride, washed with saturated aqueous sodium chloride and dried over sodium sulfate. Upon evporation and crystallization from ethanol-ether there is obtained 10.3 g rac-1,2,2,3-endo-Tetramethyl-7-anti-amine-norbornane hydrochloride, melting above 300° C.

The starting material used in the above process may be obtained, in a manner analogous to that set forth in Example 8, from rac-3-endo-amino-1,4,7,7-tetramethyl-2-exo-norbornanol (m.p. 218°–220° C). This amino compound is reacted with formic acid methyl ester, in the presence of catalytic amounts of formic acid, to form rac-N-(2-exo-hydroxy-1,4,7,7-tetramethyl-3-endo-norbornyl)formamide (m.p. 169°–171° C, upon crystallization from ethanol/n-hexane). This formamido compound is treated, in ether, with thionyl chloride and afterwards with a mixture of isopropanol and water (3:1). There is thus obtained rac-1,2,2-trimethyl-3-methylene-7-anti-amino-norbornane hydrochloride (m.p. 263°–265° C). The corresponding hydroacetate melts at 141°–143° C).

Tablets of the following composition are manufactured in the usual manner:

| | |
|---|---|
| Rac-2,2,3-endo-trimethyl-7-anti-amino-norbornane | 50 mg |
| Lactose | 89 mg |
| Maize starch | 50 mg |
| Pregelatinized lactose | 8 mg |
| Calcium stearate | 3 mg |
| Total Weight | 200 mg |

EXAMPLE 11

Capsules containing the following ingredients are manufactured in the usual manner:

| | |
|---|---|
| Rac-2,2,3-endo-trimethyl-7-anti-amino-norbornane hydrochloride | 50 mg |
| Lactose | 150 mg |
| Talc | 10 mg |

We claim:
1. A compound of the formula

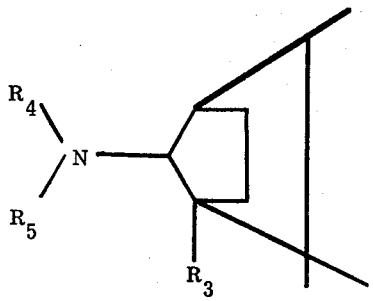

(III)

wherein R₃ is hydrogen atom or methyl, R₄ is hydrogen or a protecting group cleavable by solvolysis or reduction and R₅ is a protecting group cleavable by solvolysis or reduction and the optically active enantiomers and acid addition salts thereof wherein said protecting groups cleavable by solvolysis and reduction are selected from the group consisting of benzyl, carboalkoxy, carbobenzoxy, and formyl.

2. 2,2,3-Endo-trimethyl-7-anti-(p-toluene-sulphonylamide)-norbornane.

3. 7-Anti-(p-toluenesulphonylamido)-camphene.

4. 2,2-Dimethyl-3-endo-hydroxymethyl-7-anti-(p-toluenesulphonylamido)-norbornane.

5. 2,2-Dimethyl-3-endo-(p-toluenesulphonyloxymethyl)7-anti-(p-toluenesulphonyl-amido)-norbornane.

* * * * *